United States Patent [19]

Farrar et al.

[11] Patent Number: 4,955,874
[45] Date of Patent: Sep. 11, 1990

[54] DRAINAGE DEVICE

[75] Inventors: Quinton J. Farrar; Frederick A. Everett, Jr., both of Lakeville, Mass.; Richard H. Heimann, Flushing, N.Y.

[73] Assignee: Pfizer Hospital Products Group, Inc., New York, N.Y.

[21] Appl. No.: 249,808

[22] Filed: Sep. 27, 1988

[51] Int. Cl.⁵ ............................................ A61M 1/00
[52] U.S. Cl. ...................................... 604/319; 137/205
[58] Field of Search ......... 137/205; 604/317, 319–321

[56] References Cited

U.S. PATENT DOCUMENTS

| | | | |
|---|---|---|---|
| 3,783,870 | 1/1974 | Schachet | 604/321 |
| 4,245,637 | 1/1981 | Nichols | 604/320 |
| 4,430,085 | 2/1984 | Ahrons | 604/321 |
| 4,439,189 | 3/1984 | Sargeant et al. | 604/321 |
| 4,772,277 | 9/1988 | Schiller | 604/321 |
| 4,781,707 | 11/1988 | Boehringer et al. | 604/319 |
| 4,784,642 | 11/1988 | Everett et al. | 604/320 |

Primary Examiner—J. L. Kruter
Attorney, Agent, or Firm—Peter C. Richardson; Lawrence C. Akers; John L. LaPierre

[57] ABSTRACT

A drainage device, particularly adapted for use in medical procedures for draining fluids from a body cavity of a patient, incorporating a suction control chamber dimensioned and configured to provide an enhanced air and liquid flow pattern within the chamber. The suction control chamber might also include a baffle plate for air and noise control. The drainage device might further include a seal chamber and an improved high negativity relief valve. The present invention also includes a device, having an integral sampling or injection port, for coupling tubing.

40 Claims, 4 Drawing Sheets

DRAINAGE DEVICE

BACKGROUND OF THE INVENTION

The present invention pertains generally to drainage devices for use in the removal of fluids, such as liquids and gases, from body cavities of medical patients. More particularly, the invention relates to suction drainage systems which incorporate an improved suction control chamber for governing the flow pattern of air and liquid within the chamber. The present invention also includes a valve for maintaining desired pressure levels in a collection chamber of a drainage device. Furthermore, the invention includes a tube coupling device having a sample collection or injection port.

There have been a number of patient drainage devices introduced into the marketplace over the years. Typically, a drainage system incorporating a water filled manometer in the suction control chamber is connected to a central vacuum supply line in a hospital to provide a source of suction pressure. The suction permits withdrawal of fluids, such as blood, water and gas, from a patient's pleural cavity by establishing a pressure differential between the suction source and the internal pressure in the patient. Suction pressure and pressure differentials must be controlled to avoid harm to the patient should unduly high or low pressure differentials occur. However, since the hospital suction source is not typically constant, the degree of suction imposed on the drainage device varies. Therefore, there exists a need for regulating the degree of vacuum maintained in the collection chamber of the drainage device.

A number of wet suction control drainage devices have been introduced to regulate the pressure in the collection chamber through use of a water filled manometer in the suction control chamber. Devices of this type can be found, for example, in U.S. Pat. Nos. 3,559,647; 3,683,913; 4,439,190; and 4,465,483, to mention but a few. Despite the general acceptance of wet suction control drainage devices in the medical community, there remains a continuing need to improve the convenience and performance of chest drainage systems and to render such systems compact.

Typically, wet suction control drainage devices incorporating a water filled manometer, in use, draw gas, typically air, into and up through the water in the large arm of the manometer. The gas drawn into the system causes turbulence in the water and raises the water level. If the source of suction is sufficiently high, turbulence is increased and water can be lifted and spilled over into the next chamber of the device. Also, a high degree of turbulence could increase the rate of evaporation of water from the suction control chamber. Either situation would require water replacement if predetermined pressure levels are to be maintained. To control spillover and evaporation, some devices have employed flow directional guides in the large arm portion of the manometer. The guides, in effect, direct the gas and water by imparting a rotational or swirling motion to the gas and water body. However, such a body motion can drive the gas into the water instead of directing the gas up and out of the chamber. This condition might result in increased dispersion and entrainment of gas in the water, increased water lift, and increased rate of water evaporation.

We have invented an improved drainage device which provides additional improvements to presently available devices. The levels of suction obtained by a water controlled chest drainage system are somewhat limited by the size of the monometer tube required to maintain such suction levels. For high levels of suction, the size of manometer required would in some circumstances render the drainage system impractical. An obvious approach to solving the water spillover problem would be to increase the overall height of the drainage unit. Here we have reduced the unit height rendering the unit more compact. Another approach, aimed at reducing the effect of evaporation, would be to increase water volume. Here we have maintained the water volume at a convenient level of 500 cubic centimeters and reduced the evaporation rate. We have achieved these results by improving the gas flow pattern through the suction control chamber which reduces turbulence in the chamber. The resulting major improvements are reduction in water evaporation rate, virtual elimination of water spillover from the suction control chamber, lower noise levels, and higher gas flow capabilities.

In the chamber of the drainage device used to collect fluids drained from the plural cavity, it is possible to develop below normal pressure levels. These below normal pressure levels could result from a patient vigorously coughing, from forced inspiration caused by an upper airway obstruction, and from the stripping of the drainage tube. In the event of below normal pressure levels, it is desirable to restore the pressure to a normal level. Accordingly, we have developed a unique negativity relief valve to restore normal pressure. Although there have been a number of different approaches followed to achieve this goal, the valve we have developed requires fewer parts and fewer process manufacturing steps.

During the drainage procedure, it is at times advantageous or desirable to draw a fresh sample of fluid drainage from the patient for testing procedures. Also, it might be advantageous to inject fluids, such as anticoagulant or medication into the drawn fluid before return of the fluid to the patient during a reinfusion procedure. According to currently available methods for obtaining drainage samples, some chest drainage devices include a resealable site in the collection chamber. However, with this method one cannot obtain a fresh sample unless the sample is withdrawn during the initial drainage procedure since the collection chamber invariably would contain fluids that have collected over a period of time. Nor does such a resealable site allow for the infusion of any drugs into the patient. Another common method is to sample directly through the patient tubing which is typically formed of latex. Although manufacturers of latex tubing claim that the latex tubing is self-sealing, tests have indicated that leakage occurs under normal operating conditions. Another disadvantage with such a sampling/injection method is the possibility that the needle of a hypodermic needle may pass through both walls of the tubing and possibly stick and injure a clinican's skin. The risk of blood contact by the clinician would therefore exist everytime a sample is withdrawn or injected into the latex tubing. Accordingly, we have invented a tube coupling apparatus which permits both fresh sample withdrawal and medication injection at a common site using a hypodermic needle without the danger of tube damage and the associated risks.

SUMMARY OF THE INVENTION

The present invention is directed toward a drainage device comprising a housing; at least one inlet in the housing adapted to be connected to a patient for draining fluids from the patient; at least one outlet in the housing adapted to be connected to a souce of suction; at least one collection chamber formed within the housing for receiving the fluids; and a suction control chamber formed within the housing and adapted to receive a predetermined volume of liquid for regulating the degree of vacuum imposed in the collection chamber, means for connecting the suction control chamber with ambient, the suction control chamber being in fluid flow communication with the collection chamber and including a minor arm portion; a major arm portion; and a passageway proximate a first end of the major arm portion connecting the arm portions and providing fluid flow communication there between, with at least a segment of the major arm portion being generally funnel-shaped. Preferably, the segment is generally a rectangular shaped funnel and the cross-sectional area of the passageway is at least about equal to the maximum transverse cross-sectional area of the minor arm portion. The drainage device might further include an underwater seal chamber formed within the housing and being in fluid flow communication with the suction control chamber and with the collection chamber, the underwater seal chamber including means for preventing passage of ambient into the collection chamber.

Also provided is a valve means for selectively connecting the collection chamber with ambient. Preferably, the valve means comprises a base member formed integrally with a wall of the collection chamber and includes at least one aperture disposed therein, a filter member, a resilient member, and a cover member having a port, the cover member being coupled to the base member retaining the filter member and the resilient member there between, with a first portion of the resilient member being accessible through the port and with a second portion of the resilient member adapted for compression between the base member and the cover member. The valve means in a first position operatively seals the collection chamber from ambient, the second portion of the resilient member being compressed to establish the seal. The valve means in a second position operatively connects the collection chamber with ambient, the first portion of the resilient member being compressed to establish the connection.

Preferably, the major arm portion of the drainage device comprises a plurality of sections with the volume of each section progressively increasing in a direction away from the passageway. Also preferred is a major arm portion having at least three sections. The sections comprise a first section having a first volume, a second section having a second volume greater than the first volume, and a third section having a volume greater than the second volume. Preferably, the second volume is about equal to or greater than two times the first volume, the third volume is about equal to or greater than the sum of the first and second volumes, and the third volume is about equal to or greater than two times the second volume.

In a preferred configuration, the first and third sections are substantially of constant transverse cross section throughout the length of the first and third sections, the second section being of variable transverse cross section throughout the length of the second section. Preferably, the transverse cross section of the second section increases in a direction away from a first end proximate the passageway with the second section including at least one wall diverging in a direction away from the first end. The combined total volume of the three sections ranges from about 400 to about 2000 cubic centimeters, with the total volume being preferably about 900 cubic centimeters.

The device of the present invention further includes in the third section means for preventing passage of the liquid from the suction control chamber into the collection chamber. The means might be an arcuate or a straight deflector plate spaced from the liquid prior to device operation. Preferably, the plate has a downwardly directed slope in the range of from about 20 to about 40 degrees with the slope being preferably about 30 degrees. The plate forms an outlet opening of preferably not less than about 0.03 square inches at a second end of the major arm portion.

Also included within the scope of the invention, disposed at a first end of the large arm portion of the drainage device, is a chamber designed and configured to support a baffle. Preferably, the baffle comprises a plate-like structure having a plurality of spaced slots disposed therein.

The invention further embodies an apparatus for draining fluids from a body cavity of a patient comprising a housing having at least one collection chamber formed therein for collecting the fluids, the collection chamber including at least one inlet adapted to establish fluid communication between the patient and the collection chamber for conveying the fluids into the collection chamber, at least one outlet in the housing adapted to be connected to a source of suction, and a suction control chamber in fluid flow communication with ambient and with the collection chamber and adapted to receive a predetermined volume of liquid regulating the degree of vacuum imposed in the collection chamber, the suction control chamber having a minor arm portion, a major arm portion, and means for establishing fluid flow communication between arm portions, with the major arm portion comprising at least three sections with the volume of each section progressively increasing in a direction away from the communicating means.

In addition, the present invention is directed toward a tube coupling apparatus comprising a hollow elongated member at a first end adapted to be connected to a first tube, with the member at a second end adapted to be connected to a second tube to provide a passageway interconnecting the first and second tubes, and with the member including a port disposed therein to provide access to the passageway unobstructed by either of the tubes. In another embodiment, the coupling comprises a first hollow elongated member at a first end adapted to be connected to a first tube, a second hollow elongated member at a first end adapted to be connected to a second tube, and means for coupling second ends of the members to provide a passageway interconnecting the first and second tubes, with one of the members including a port disposed therein to provide access to the passageway unobstructed by either of the tubes. Preferably, the port is filled with a self sealing elastomeric material under compression to seal the passageway from ambient and to permit insertion of a hypodermic needle into the passageway to withdraw fluid therefrom or to inject the contents of the needle therein. The elastomeric material is preferably latex.

DETAILED DESCRIPTION OF THE PREFERRED EMBODIMENTS

Figure 1:
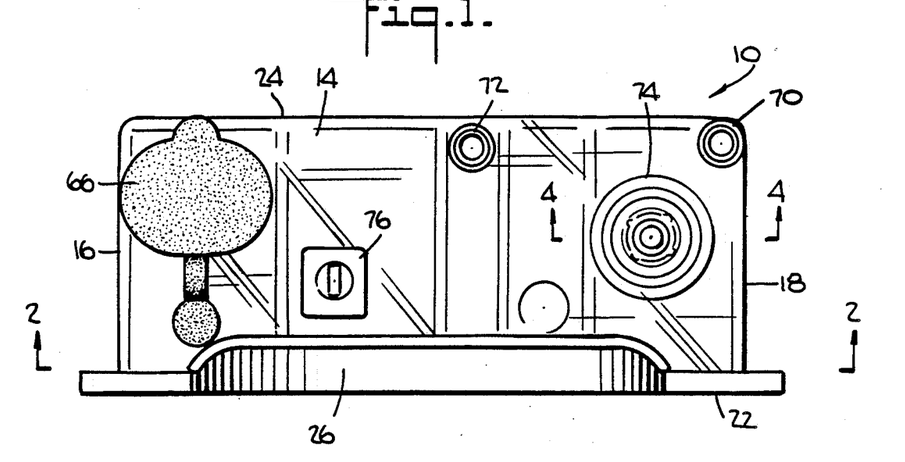
FIG. 1 is a top plan view of a drainage device in accordance with the principles of the present invention.
Figure 2:
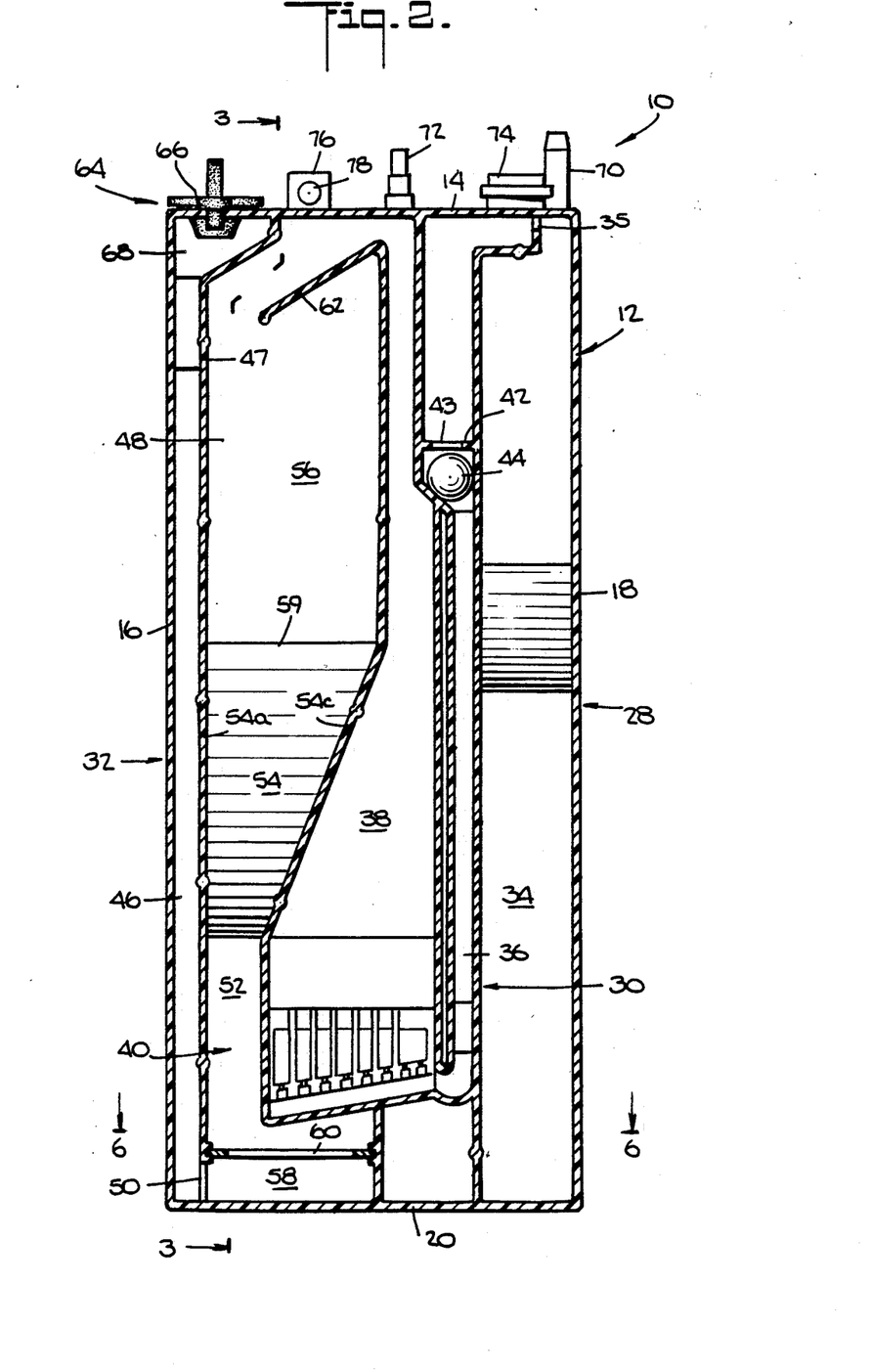
FIG. 2 is a sectional view, drawn at a slightly reduced scale, taken along line 2—2 of the drainage device illustrated in FIG. 1, but not showing the front wall of the device.
Figure 3:
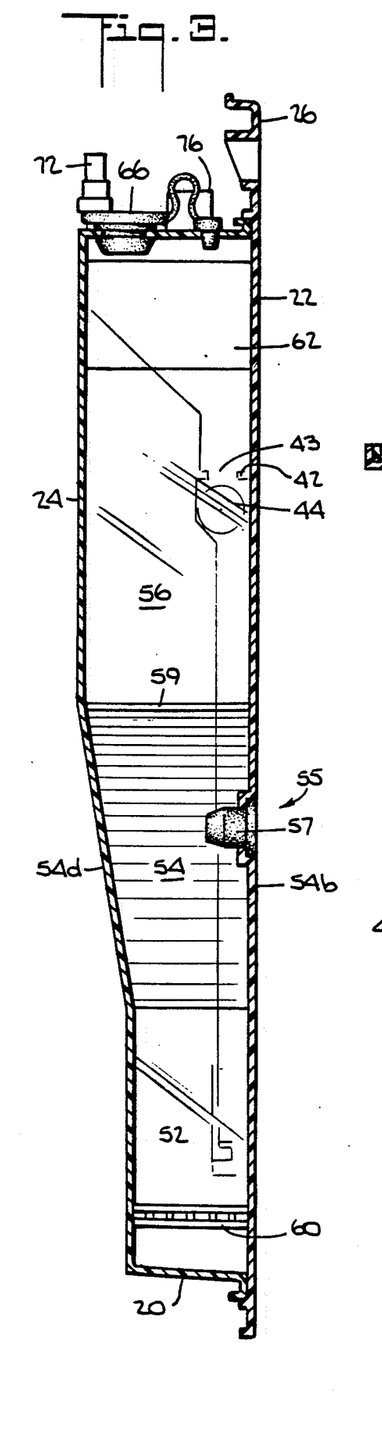
FIG. 3 is a sectional view, slightly enlarged, taken along line 3—3 of the device shown in FIG. 2, but including the front wall of the device.

The description herein presented refers to the accompanying drawings in which like reference numerals refer to like parts throughout the several views. Referring to FIGS. 1-3, in accordance with the principles of the present invention, there are illustrated plan and cross-sectional views of a chest drainage device 10 comprising a housing 12 having top wall 14, side walls 16 and 18, bottom wall 20, front wall 22 and rear wall 24. A handle 26 is incorporated into front wall 22. The device 10 is shown with three chambers, namely, a collection chamber 28 for receiving and storing fluids collected from a body cavity, a water seal chamber 30 for preventing any liquid from entering into the collection chamber during high levels of negative pressure in the body cavity, and a wet suction control chamber 32 for regulating the degree of suction maintained in the collection chamber. The function and operation of these chambers are generally described in U.S. Pat. Nos. 3,559,647; 3,683,913; 4,018,224; and U.S. Pat. No. Re. 29,877 to the extent that like or common elements are presented therein. The disclosures of these patents are incorporated herein in their entirety. It should be understood, however, that device 10 would be fully functional as a two chambered device, that is, with a suction control chamber and a collection chamber. The water seal chamber has been included in one embodiment of the invention.

Collection chamber 28 is shown as having a single compartment 34 but it should be understood that, as desired, a plurality of compartments and more than one collection chamber are also contemplated to be within the scope of the invention. Water seal chamber 30 is shown to include a small arm compartment 36 a large compartment 38, and an air flow meter 40. Communication between small arm compartment 36 and collection chamber compartment 34 is established through opening 35. Air flow meter 40 is of the type illustrated and described in aforementioned U.S. Pat. No. 3,683,913 whose disclosure is incorporated herein in its entirety. Small arm compartment 36 further includes a valve mechanism comprising a plate member 42 having an opening 43 and a ball float valve 44 that is free to travel between plate member 42 and a constricted portion of small arm compartment 36 as shown in FIG. 2. In operation under suction, ball float valve 44 will not block off the lower portion of small arm compartment 36.

Suction control chamber 32 includes a minor arm portion 46, a major arm portion 48 and a passageway 50 connecting the minor and major arm portions. Major arm portion 48 has a number of segments or sections comprising throat 52, expansion thank 54, and surge tank 56. A grommet 55 is provided in front wall 22 so as to permit injection of fluid, if desired, into expansion tank 54. Similarly, in order to allow for filling of water seal chamber 30, another grommet (not shown) is provided in front wall 22 so as to permit injection of fluid into large compartment 38. The grommets include a central rubber portion 57 which permit injection of fluid by means of a hypodermic needle which will penetrate, but not damage, the rubber seal that thereafter self-seals and retains the integrity of the respective chambers or portions thereof. In one embodiment, major arm portion 48 might include a baffle chamber 58, located below throat 52, designed and configured to support a baffle plate 60 having slots 61. Chamber 58, functioning to reduce noise and to disperse air, is positioned below water seal chamber 30 to aid in optimizing unit compactness. In another embodiment, a deflector plate 62 might be positioned above surge tank 56. Minor arm portion 46, at the end opposite passageway 50, includes an ambient or atmospheric vent generally designated 64 wherein a combined muffler and cap 66 is tethered to housing 12 along top wall 14 and is inserted into an opening (not shown) in the top wall. The term ambient, as used herein throughout, means the surrounding atmosphere or environment. The atmospheric vent is used for filling the suction control chamber. The muffler/cap acts to absorb sound, prevents objects from falling into the suction control chamber, and prevents objects from occluding the vent. When the muffler/cap has been seated, a tortuous fluid flow path is established to allow ambient gas (usually atmospheric air) to enter the device. A segment 68 of minor arm portion 46 immediately below cap 66 has been configured to receive and direct water or other suitable liquid into suction control chamber 32 prior to operation of drainage device 10.

In drainage device 10, housing 12 further includes an inlet 70 adapted to be connected to a patient via tubing (not shown) connected to the inlet for draining fluids from the patient and into collection chamber 28. Additionally, housing 12 includes an outlet 72 adapted to be connected to a source of suction (not shown) via tubing (not shown) for imposing a negative pressure in collection chamber 28.

The drainage device might further include a high negativity relief valve 74, shown positioned in top wall 14, in communication with collection chamber 28. It should be understood that valve 74 could be suitably located in another of the housing walls. The high negativity relief valve may be activated to relieve undesirable high degrees of negative pressure that may occur in the body cavity and thereby develop in the collection chamber. Design and operation of valve 74 are shown in greater detail in FIGS. 4 and 5 and are described below in more detail. Additionally, the device might further include a positive pressure relief valve 76, including valve member 78. Valve 76 is of the check type configuration which is normally closed during device operation but it functions to open to permit excessive pressure in seal chamber 30 (or suction control chamber 32 in devices without a seal chamber) to be vented to the ambient or atmosphere in response to any substantially increased pressure within the seal chamber 30 (or suction control chamber 32).

At least one of the segments of major arm portion 48 of suction control chamber 32 is generally funnel-shaped. Here, upon viewing FIGS. 2 and 3, it can readily be observed that expansion tank 54 is generally funnel-shaped and, more particularly, a funnel of generally ractangular configuration. Walls 54a, 54b are generally straight while walls 54c, 54d slope upwardly and outwardly as one progresses through expansion tank 54. The term funnel, as used herein throughout, means a hollow element in the form of a cone, triangle, quadrilateral, polygon, or the like, having ends of unequal cross section, with a constricted area extending from the smaller end of the structure, and that is designed to direct fluid flow. Here the flow is upwardly from the constricted end to the enlarged end of the section.

In operation, water in minor arm portion 46 is displaced by atmospheric air into major arm portion 48 where bubbling occurs. The suction pressure level in collection chamber 28 is controlled by the water height in major arm portion 48. Throat section 52, preferably of constant cross sectional area, positions the air bubble stream in relation to expansion tank 54 and surge tank 56. The throat is sized such that it does not cause restriction or back pressure and allows the air bubbles to pass freely therethrough and into expansion tank 54. The depth and width of expansion tank 54 increases throughtout its length. As air moves through throat section 52 and then the lesser volume of the lower end of expansion tank 54, it displaces water upwardly through expanding tank 54 which tank, as it progressively increases in area, tends to reduce upward lift of the water. The configuration of tank 54 acts as a funnel which feeds displaced fluid back behind the upper flow, imparting rotational motion to the fluid and reducing total upward displacement and turbulence. The expansion tank configuration avoids dead spaces in the flow pattern and the given upward displacement per unit volume throughput is continually replenished. The elimination of dead space is conducive to uniform flow, to lesser turbulence, and to lesser upward fluid displacement. Positioned above expansion tank 54 is surge tank 56 which is preferably constant in cross sectional area and which section has a cross sectional area at least equal to that at the enlarged end of the expansion tank and a volume greater than that of either the throat section or the expansion tank.

Under typical operating conditions, before device usage, the water level in major arm portion 48 is filled to just past junction 59 between expansion and surge tank sections. The advantage to this height volume relationship is that the maximum cross sectional area is achieved at the water air transition zone while having only a minimal impact on the fill volume. The relatively large cross sectional area provides for an excellent dispersion of air bubbles at the water surface. Since in many cases up to 50 liters per minute of air is passed through a controlling fluid volume of 0.5 liters, there is a need for a surge capacity at the top of major arm portion 48. The overall configuration of major arm portion 48 allows air to be channeled through the arm portion with little additional resistance to escaping air and with no downward deflection of air.

In a preferred embodiment, defector plate 62, positioned above surge tank 56, along its underside presents an upward barrier to spray from bursting bubbles. The space between divider wall 47 of minor arm portion 46 and deflector plate 62 is sufficiently wide so as not to increase the velocity of air moving through the space and thus carrying water over into the next chamber. The deflector plate design is such that the force of gravity will pull fluid droplets to the lowermost edge of the plate and allow the droplets to fall back into the surge tank.

Figure 4:
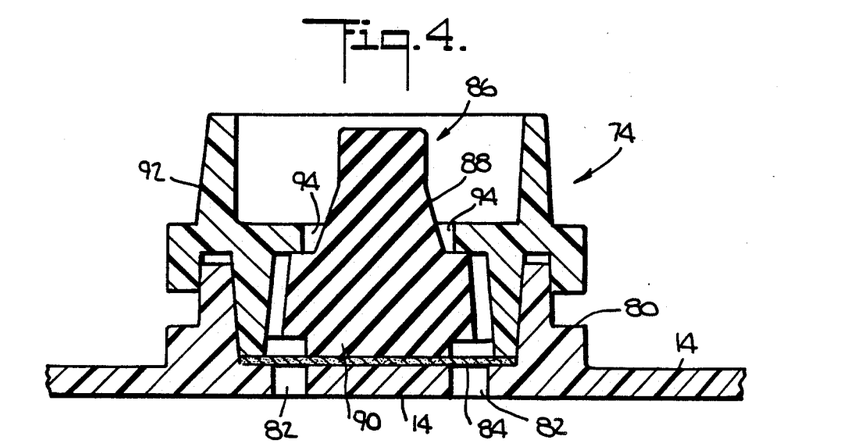
FIG. 4 is an enlarged partial cross-sectional view, taken along line 4—4 of the drainage device depicted in FIG. 1, showing a negative pressure relief valve at rest.
Figure 5:
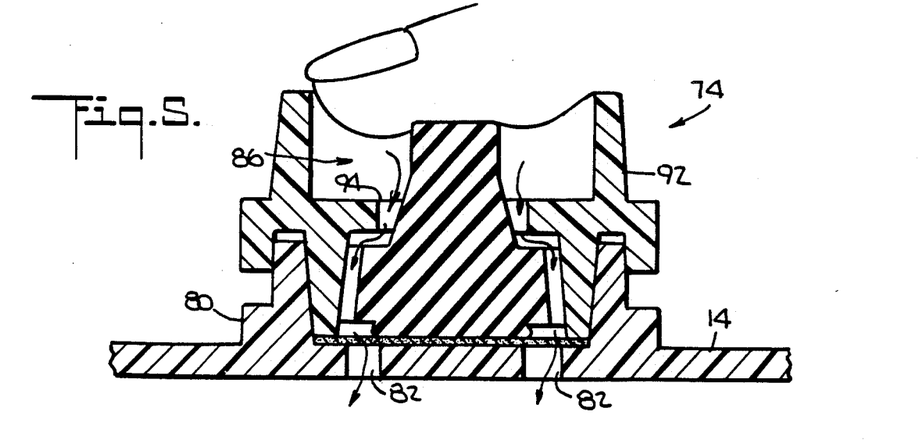
FIG. 5 is a cross-sectional view of the negative pressure relief valve shown in FIG. 4 but showing the valve in an activated position.

Turning now to FIGS. 4 and 5, detail of high negativity relief valve 74 will now be discussed. Valve 74 comprises a base member 80 formed integrally with top wall portion 14 of collection chamber 28, base member 80 including at least one aperture 82 disposed therein, a filter member 84, a resilient member 86 of rubber or like substance having portions 88 and 90, and a cover member 92 which includes port 94. It should be understood that the location of base member 80 is not limited to top wall portion 14 but may be located in another wall of the collection chamber as desired. Cover member 92 and base member 80 are coupled together to retain filter member 84 and resilient member 86 there between. Portion 88 of resilient member 86 is accessible through port 94. Preferably, cover member 92 extends above portion 88 of resilient member 86 to guard against inadvertent valve activation. Portion 90 of resilient member 86 is compressed between base member 80 and cover member 92 closing port 94 to seal collection chamber 28 from ambient as shown in FIG. 4. In FIG. 5, there is shown valve 74 being manually activated by the depression of portion 88 of resilient member 86. When portion 88 is depressed or compressed, portion 90 is further compressed to open port 94. The opening of port 94 allows ambient air at a higher pressure to flow around resilient member 86, through filter member 84 and through aperture 82, and into the collection chamber. The ambient air flow path is shown by the arrows in FIG. 5. Port 94 is maintained in an open position for a time sufficient to allow filtered air to enter the collection chamber to restore the desired level of pressure in the collection chamber.

Figure 6:
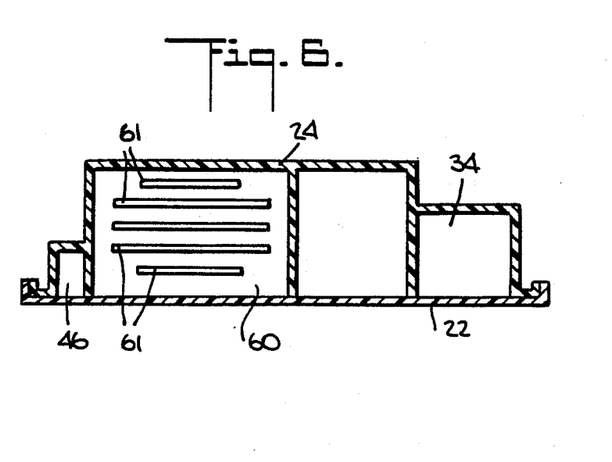
FIG. 6 is a cross-sectional view, enlarged slightly, taken along line 6—6 of the drainage device depicted in FIG. 2, but including the front wall of the device.
Figure 7:
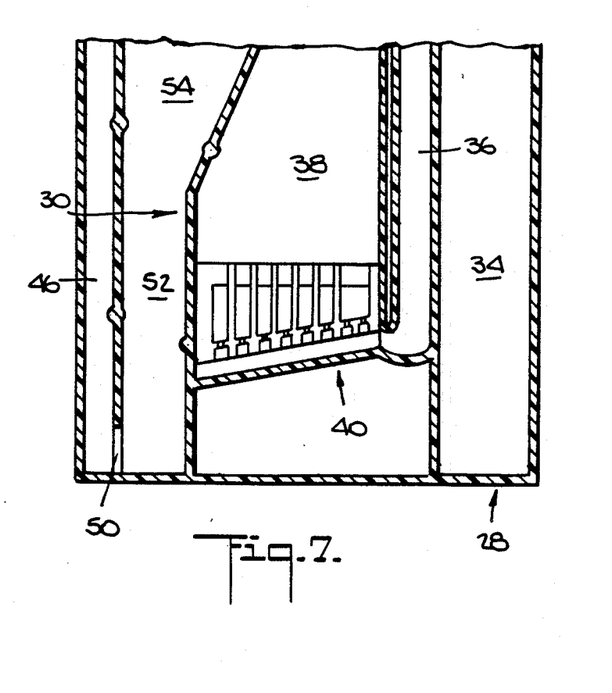
FIG. 7 is a partial modified view of the lower portion of the drainage device illustrated in FIG. 2.

The illustration of FIG. 6 is provided to indicate the detail of baffle plate 60 having slotted openings 61. Another embodiment of device 10 is shown in FIG. 7 wherein the chamber 58 and baffle 60 structure of FIG. 2 have been eliminated. The device is functional without the inclusion of these elements. Likewise, the device would be operational without water seal chamber 30. Of course, in a most preferred form of the invention, the device would include water seal chamber 30, chamber 58 and baffle plate 60.

Figures 8, 9:
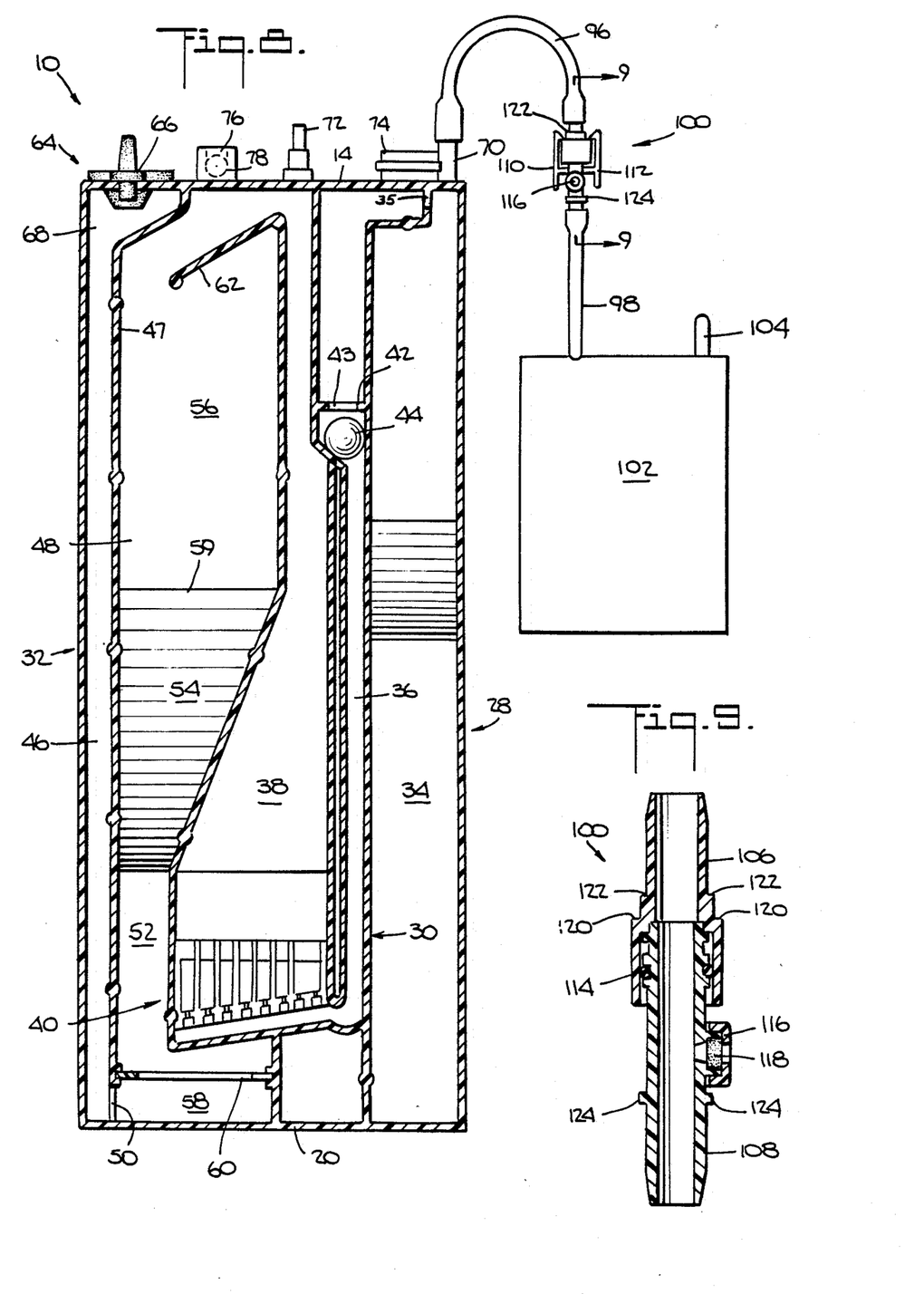
FIG. 8 is a view, similar to that shown in FIG. 2, illustrating a tube coupling device having a sample collection or injection port.
FIG. 9 is a partial sectional view taken along line 9—9 of the tube coupling device shown in FIG. 8.

Turning now to FIG. 8, there is shown drainage device 10 having all of the structure of the device depicted in FIGS. 2 and 3. However, inlet 70 is not now directly connected to a patient but is instead connected to a first tube 96 which is coupled to a second tube 98 by means of a tube coupling apparatus 100. Tube 98 is connected to a blood collection reservoir designated generally as 102 and it is blood reservoir 102 via inlet 104 and tubing connected thereto, but not shown, that is in direct communication with the patient. Outlet 72 is still to be connected to a source of suction but now collection reservoir 102 first receives the fluid and gas collected from the patient.

Upon viewing FIGS. 8 and 9, there can be seen that coupling apparatus 100 includes hollow elongated members 106 and 108, coupling arms 110 and 112, sealing O-ring 114, and sampling/injection port 116 which includes latex sealing material 118. Elastomeric material 118, which is under compression, is capable of withstanding multiple hypodermic needle punctures while maintaining its self-sealing capability. As shown in FIG. 9, member 108 is received partially within member 106. Member 108 is customarily termed a male coupling member and member 106 is customarily termed a female coupling member. Sealing O-ring 114 maintains a tight seal betwen members 106 and 108 and arms 110 and 112 engage ledge 120 to maintain the members in a locked coupled position. Ledges or stop means 122 and 124 prevent tubes 96 and 98, respectively, from being advanced beyond the stop means as tubes 96 and 98 are drawn over the ends of members 106 and 108. Tubes 96 and 98 are not shown in FIG. 9 but it should be understood that an end of members 106 and 108 is adapted to receive the respective tube. The coupling of members 106 and 108 can be released by disengaging arms 110 and 112 from ledge 120 and pulling the members apart. While there is herein shown a multiple piece coupling assembly, it is contemplated to be within the scope of the invention, although not shown, that a single hollow elongated member with a sample/injection port could replace members 106 and 108.

The location of sampling/injection port 116 is a distance removed from the ends of tubes 96 and 98. Thus sampling or injection can take place using a needle without puncturing the tubes. Additionally, the structural property of member 108 is such that a needle entering port 116 will not pass through the rear wall of the member. Therefore, the risk of tube puncturing and leaks and the risk of passing a needle through the device and into one's skin have been eliminated.

The present invention has been described herein with specific reference to the preferred embodiments thereof. However, those skilled in the art will understand that changes may be made in the form of the invention covered by the claims without departing from the scope and spirit thereof, and that certain features of the invention may sometimes be used to an advantage without corresponding use of the other features.

We claim:
1. A drainage device comprising
   a housing;
   at least one inlet in said housing adapted to be connected to a patient for draining fluids from said patient;
   at least one outlet in said housing adapted to be connected to a source of suction;
   at least one collection chamber formed within said housing for receiving said fluids; and
   a suction control chamber formed within said housing and having a vertical longitudinal axis and adapted to receive a predetermined volume of liquid for regulating the degree of vacuum imposed in said collection chamber, means for connecting said suction control chamber with ambient, said suction control chamber being in fluid flow communication with said collection chamber and including
   a minor arm portion;
   a major arm portion; and
   a passageway proximate a first end of said major arm portion connecting said arm portions and providing fluid flow communication there between, with at least a segment of said major arm portion, having more than one upwardly diverging wall with respect to said axis and being downstream of said small arm, being designed and configured generally of funnel shape in full transverse sections along said axis.

2. The drainage device according to claim 1 wherein said segment is generally a rectangular shaped funnel.

3. The drainage device according to claim 1 further including an underwater seal chamber formed within said housing and being in fluid flow communication with said suction control chamber and with said collection chamber, said underwater seal chamber including means for preventing passage of said ambient into said collection chamber.

4. The drainage device according to claim 1 further including valve means for selectively connecting said collection chamber with ambient.

5. The drainage device according to claim 4 wherein said valve means comprises a base member formed integrally with said collection chamber and including at least one aperture disposed therein, a filter member, a resilient member, and a cover member having an opening, said cover member being coupled to said base member securing said filter member and said resilient member there between, with a first portion of said resilient member being accessible through said opening and with a second portion of said resilient member being compressed between said base member and said cover member.

6. The drainage device according to claim 1 wherein the cross-sectional area of said passageway is at least about equal to the maximum transverse cross-sectional area of said minor arm portion.

7. The drainage device according to claim 1 wherein said major arm portion comprises a plurality of sections with the volume of each section progressively increasing in a direction away from said passageway.

8. The drainage device according to claim 7 wherein said major arm portion comprises at least three sections.

9. The drainage device according to claim 8 wherein said sections comprise a first section having a first volume, a second section having a second volume greater than said first volume, and a third section having a third volume greater than said second volume.

10. The drainage device according to claim 9 wherein said second volume is about equal to or greater than two times said first volume.

11. The drainage device according to claim 9 wherein said third volume is about equal to or greater than the sum of said first and said second volumes.

12. The drainage device according to claim 9 wherein said third volume is about equal to or greater than two times said second volume.

13. The drainage device according to claim 9 wherein said first and said third sections are substantially of constant transverse cross section throughout the length of said first and said third sections, said second section being of variable transverse cross section throughout the length of said second section.

14. The drainage device according to claim 13 wherein the transverse cross section of said second section increases in a direction away from a first end proximate said passageway.

15. The drainage device according to claim 14 wherein said second section includes at least one wall diverging in a direction away from said first end.

16. The drainage device according to claim 9 wherein the combined total volume of said first, second and third sections is in the range of from about 400 to about 2000 cubic centimeters.

17. The drainage device according to claim 16 wherein said total volume is preferably about 900 cubic centimeters.

18. The drainage device according to claim 9 wherein said third section further includes means for preventing passage of said liquid from said suction control chamber into said collection chamber.

19. The drainage device according to claim 18 wherein said means is an arcuate deflector plate.

20. The drainage device according to claim 18 wherein said means is a generally straight deflector plate.

21. The drainage device according to claim 20 wherein said plate is spaced from said liquid prior to operation of said device.

22. The drainage device according to claim 21 wherein said plate has a generally downwardly directed slope.

23. The drainage device according to claim 22 wherein said slope is in the range of from about 20 to about 40 degrees.

24. The drainage device according to claim 23 wherein said slope is preferably about 30°.

25. The drainage device according to claim 20 wherein said plate forms an outlet opening of not less than about 0.03 square inches at a second end of said major arm portion.

26. A drainage device adapted to be connected to a body cavity of a patient comprising a housing having an inlet and an outlet, a collection chamber, and a suction control chamber, said suction control chamber having a vertical longitudinal axis and being in fluid flow communication with ambient and with said collection chamber, said suction control chamber having a large arm and a small arm in fluid flow communication with each other, said large arm including a plurality of segments with at least one of said segments, having more than one upwardly diverging wall with respect to said axis and being downstream of said small arm, being designed and configured generally of funnel shape in full transverse sections along said axis.

27. The drainage device according to claim 26 wherein said one segment is generally a rectangular shaped funnel.

28. The drainage device according to claim 26 wherein said segments number three or more.

29. The drainage device according to claim 28 wherein said segments generally increase in volume sequentially from a first segment of least volume disposed near a first end of said large arm to a terminal segment of greatest volume disposed at a second end of said large arm.

30. The drainage device according to claim 26 further designed and configured to include a chamber at a first end of said large arm supporting a baffle.

31. The drainage device according to claim 30 wherein said baffle comprises a plate-like structure having a plurality of spaced slots disposed therein.

32. A drainage device adapted to be connected to a body cavity of a patient comprising a housing having an inlet, an outlet, a collection chamber, a suction control chamber, and valve means for selectively connecting said collection chamber with ambient, with said valve means comprising a base member formed integrally with a wall of said collection chamber and including at least one aperture disposed therein, a filter member, a resilient member, and a cover member having a port, said cover member being coupled to said base member retaining said filter member and said resilient member there between, with a first portion of said resilient member being accessible through said port and with a second portion of said resilient member adapted for compression between said base member and said cover member.

33. The drainage device according to claim 32 wherein said valve means in a first position operatively seals said collection chamber from ambient, said second portion of said resilient member being compressed to establish said seal.

34. The drainage device according to claim 32 wherein said valve means in a second position operatively connects said collection chamber with ambient, said first portion of said resilient member being compressed to establish said connection.

35. An apparatus for draining fluids from body cavity of a patient comprising a housing having at least one collection chamber formed therein for collecting said fluids, said collection chamber including at least one inlet adapted to establish fluid communication between said patient and said collection chamber for conveying said fluids into said collection chamber, at least one outlet in said housing adapted to be connected to a source of suction, and a suction control chamber, having a vertical longitudinal axis, in fluid flow communication with ambient and with said collection chamber and adapted to receive a predetermined volume of liquid for regulating the degree of vacuum imposed in said collection chamber, said suction control chamber having a minor arm portion, a major arm portion, and means for establishing fluid flow communication between arm portions, with said major arm portion comprising at least three sections with the volume of each section progressively increasing in a direction away from said communicating means and with at least one of said sections, having more than one upwardly diverging wall with respect to said axis and being downstream of said small arm, being designed and configured generally of funnel shape in full transverse sections along said axis.

36. The apparatus according to claim 35 wherein said sections comprise a first section having a first volume, a second section having a second volume greater than said first volume, and a third section having a third volume greater than said second volume.

37. The apparatus according to claim 36 wherein said second volume is about equal to or greater than two times said first volume.

38. The apparatus according to claim 36 wherein said third volume is about equal to or greater than the sum of said first and said second volumes.

39. The apparats according to claim 36 wherein said third volume is about equal to or greater than two times said second volume.

40. The apparatus according to claim 36 wherein said first and said third sections are substantially of constant transverse cross section throughout the length of said first and said third sections, said second section being of variable transverse cross section throughout the length of said second section.

* * * * *